United States Patent [19]

Ng

[11] Patent Number: 5,283,921
[45] Date of Patent: Feb. 8, 1994

[54] ELECTRIC TOOTHBRUSH HOLDER

[76] Inventor: Poon-Kee G. Ng, Room A908, 9th Floor, Block A, 2-8 Watson Road, North Point, Hong Kong

[21] Appl. No.: 887,772

[22] Filed: May 21, 1992

[30] Foreign Application Priority Data

May 21, 1991 [GB] United Kingdom ............ 9110963.7

[51] Int. Cl.⁵ ............................................. A61C 17/32
[52] U.S. Cl. ...................................... 15/22.1; 15/145; 15/176.6; 279/906
[58] Field of Search ................. 15/22.1, 22.2, 22.4, 15/176.1, 176.6, 145; 279/43.7, 46.7, 55-59, 906

[56] References Cited

U.S. PATENT DOCUMENTS

| | | | |
|---|---|---|---|
| 2,095,956 | 10/1937 | Bess | 15/22.1 |
| 2,319,205 | 5/1943 | Buck | 15/22.1 |
| 2,875,458 | 3/1959 | Tsuda | 15/22.1 |
| 3,196,299 | 7/1965 | Kott | 15/22.1 |
| 3,316,576 | 5/1967 | Urbush | 15/22.1 |
| 4,458,374 | 7/1984 | Hukaba | 15/22.1 |
| 5,029,881 | 7/1991 | Godfrey | 279/46.7 |

FOREIGN PATENT DOCUMENTS

| | | |
|---|---|---|
| 978883 | 12/1964 | United Kingdom . |
| 1080971 | 8/1967 | United Kingdom . |
| 2097663 | 11/1982 | United Kingdom . |
| 2211455 | 7/1989 | United Kingdom . |

Primary Examiner—Edward L. Roberts
Attorney, Agent, or Firm—Eckert Seamans Cherin & Mellott

[57] ABSTRACT

An electric toothbrush holder which comprises a elongate casing and an electric motor vibration unit supported within the casing, the casing forming a elongate cavity having an opening at the forward end of the casing for insertion of the handle of a toothbrush, in which opening there is provided a clamping structure having at least two clamping surfaces which are resiliently biassed together by a resilient member so as to clamp or hold a said toothbrush at its handle automatically when the toothbrush handle is inserted into the cavity through the opening.

8 Claims, 3 Drawing Sheets

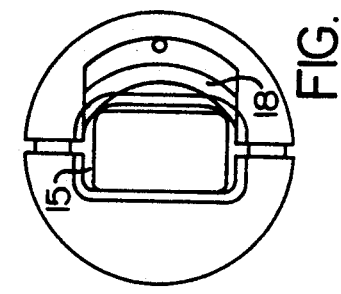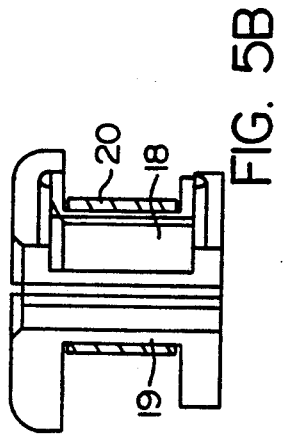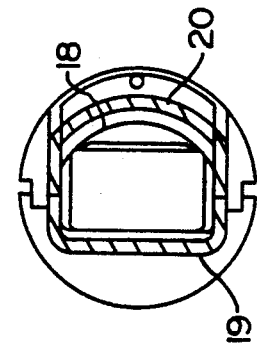
FIG. 3A  FIG. 3B  FIG. 3C
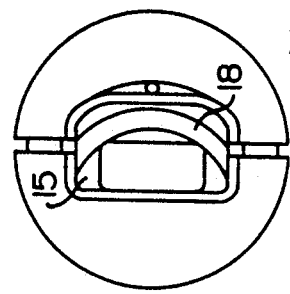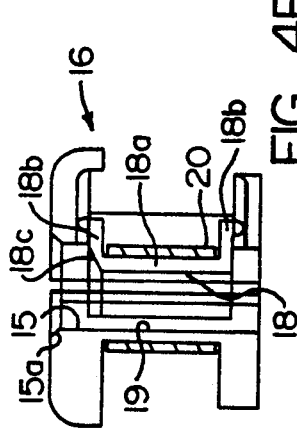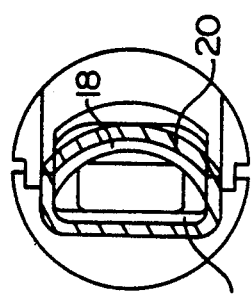
FIG. 4A  FIG. 4B  FIG. 4C
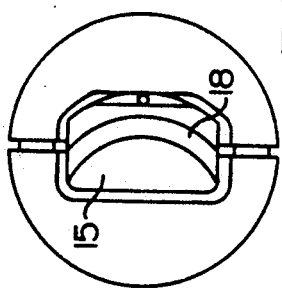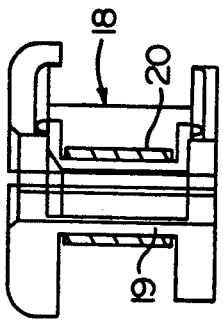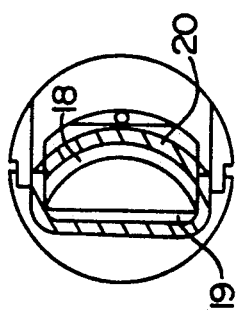
FIG. 5A  FIG. 5B  FIG. 5C

ELECTRIC TOOTHBRUSH HOLDER

BACKGROUND OF THE INVENTION

The present invention relates to an electric toothbrush holder.

Electric toothbrush holders are known and usually designed to hold interchangeably a number of toothbrushes or toothbrush heads, whether different or not, to serve different persons, or to provide different functions or to suit different operating conditions. Such toothbrushes or toothbrush heads are specially designed to be connected to a particular brand of toothbrush holders and therefore they are inevitably expensive. In addition, such toothbrushes or toothbrush heads generally have a relatively short stems, and because of this construction the connection between them and the corresponding holders are usually complicate and thus expensive for manufactury.

The invention seeks to mitigate or at least to alleviate such disadvantages.

SUMMARY OF THE INVENTION

According to the invention, there is provided an electric toothbrush holder comprising a elongate casing having a forward end and an electric motor vibration unit supported within the casing, the casing forming a elongate cavity having an opening at the forward end of the casing for insertion of the handle of a toothbrush, in which opening there is provided clamping means and a resilient member, said clamping means having at least two clamping surfaces which are resiliently biassed relatively together by the resilient member so as to clamp or hold said toothbrush at its handle automatically when the toothbrush handle is inserted into the cavity through the opening.

Preferably, said clamping means is provided by a fixed clamping element/member and a movable clamping member, the two being resiliently biassed relatively together by the resilient member.

It is preferred that the fixed clamping element/member has a flat clamping surface and the movable clamping member has a concave clamping surface facing the flat clamping surface.

In a preferred embodiment, the cavity extends from the casing forward end into the casing for a length at least one-third of the overall length of the casing.

It is an advantage that the electric toothbrush holder further comprises auxiliary clamping means which is provided at or adjacent an inner end of the cavity.

Preferably, said auxiliary clamping means comprises a leaf spring provided on one side of the cavity and co-operable with the opposite side of the cavity.

It is preferred that the vibration unit is supported by the innermost end of an internal part of the casing providing the cavity.

Preferably, the casing has an external part and an internal part, the internal part of the casing being connected to the external part of the casing at a position only at or near the outer end of the cavity.

In a preferred embodiment, the casing is formed by a forward part carrying the clamping means and a rear part carrying the vibration unit, and the electric toothbrush holder further comprises releasable engaging means for releasably engaging the forward and rear casing parts together such that the forward casing part is separable from the rear casing part for individual cleaning or washing.

Preferably, the resilient member is in the form of a rubber band disposed around the clamping means.

BRIEF DESCRIPTION OF THE DRAWINGS

The invention will now be more particularly described, by way of example only, with reference to the accompanying drawings, in which:

FIGS. 3A to 3C are fragmentary sectional forward end views of the toothbrush holder of FIG. 1;

FIGS. 4A to 4C are fragmentary sectional forward end view of the toothbrush holder of FIG. 1, holding a relatively small size toothbrush handle;

FIG. 5A to 5C are fragmentary sectional forward end views of the toothbrush holder of FIG. 1, holding a relatively large size toothbrush handle;

DETAILED DESCRIPTION OF THE PREFERRED EMBODIMENTS

Figure 1:
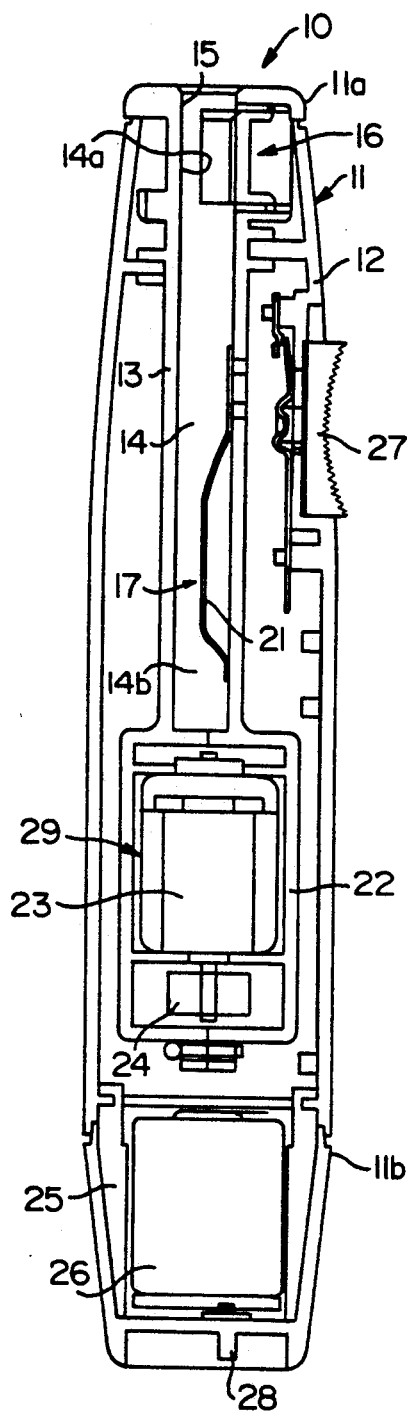
FIG. 1 is a sectional side view of a first embodiment of an electric toothbrush holder in accordance with the invention.
Figure 2:
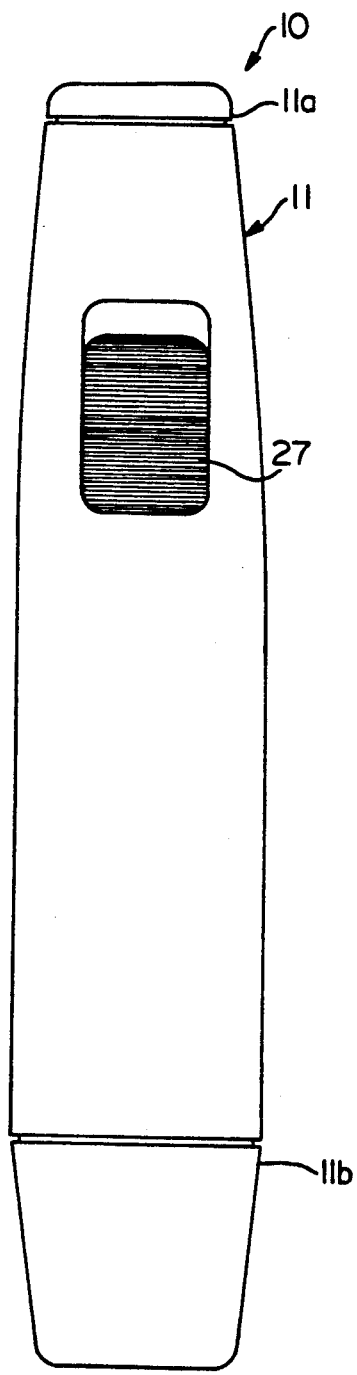
FIG. 2 is a front side view of the toothbrush holder of FIG. 1.

Referring firstly to FIGS. 1 and 2 of the drawings, there is shown a first embodiment of a toothbrush holder 10 according to the invention, which holder 10 comprises a elongate casing 11 having an inner casing wall 13 and an outer casing wall 12. The inner casing wall 13 forms a cavity 14 which has an opening 15 at the forward end 11a of the casing 11. The cavity 14 is provided for receiving an holding the stem or handle of an ordinary, full-length toothbrush (not shown but see corresponding FIG. 6). For this purpose, first and second clamping means 16 and 17 are provided at or near the outer and inner ends 14a and 14b of the cavity 14, respectively.

FIGS. 3A to 5C are also referred to. The first clamping means 16 is formed by a movable clamping member 18, a fixed clamping member 19 provided by a part of the inner casing wall 13 facing the clamping member 18, and a rubber band 20 disposed around and resiliently urging the two clamping members 18 and 19 together. The movable clamping member 18 has a part-cylindrical body 18a and two outwardly extending top and bottom flanges 18b, and provides a curved or concave clamping surface co-operable with a flat clamping surface provided by the fixed clamping member 19 to clamp a toothbrush handle. The top inner rim 18c of the clamping member 18 is chamfered, and the rim 15a of the opening 15 is also chamferd. It Will be appreciated that such chamfering facilitates the insertion of the toothbrush handle, and that the clamping means 16 will clamp or hold the toothbrush handle automatically upon insertion of the same into the cavity 14. The curved or concave shape and width of the clamping surface of the clamping member 18 serves to ensure the clamping means 16 capable of clamping most of the ordinary, commercially available toothbrushes (see FIGS. 4A to 5C), in that the said curved or concave clamping surface of the clamping member and the opposed flat clamping surface of the clamping member 19 provide three clamping points arranged in a triangular manner for stable clamping.

The second clamping means 17 is formed by a leaf spring 21 fixed on one side of the inner casing wall 13 and operable to argue a toothbrush handle inserted into the cavity 14 against the opposite side of the inner casing wall 13, whereby the free end of the toothbrush handle is also fixed.

As shown in FIG. 1 the inner casing wall 13 extends rearwardly to form at its innermost end an integral carriage 22 supporting a vibration unit 29. The vibration unit 29 is formed by a small electric motor 23 carrying on its shaft an eccentric weight 24 which upon rotation by the electric motor 23 generates a circular vibration motion. Such vibration motion is transmitted through the electric motor 23 and the inner casing wall 13 to the toothbrush held by the holder 10 so that the toothbrush head is set into a brushing motion. It can be seen from the Figure that the internal part of the casing, namely the inner casing wall 13, is connected to the external part of the casing, namely the outer casing wall 12, at a position at or near the outer end of the cavity 14 or the forward end 11a of the casing 11 but not anywhere else so that the transmission of the vibration motion of the internal assembly (13, 23 and 24) to the external casing wall 12 will be kept at a minimum.

A battery compartment 25 is provided at the rear end 11b of the casing and accommodates a rechargeable battery 26 for driving the electric motor 23. The operation of the electric motor 23 is controlled by a slide switch 27 which is provided on the front side of the casing 11 (see FIG. 2). The terminals of the rechargeable battery 26 is exposed at the casing rear end 11b, in the form of a plug 28, for connection to a separate battery charger stand (now shown).

Figure 6:
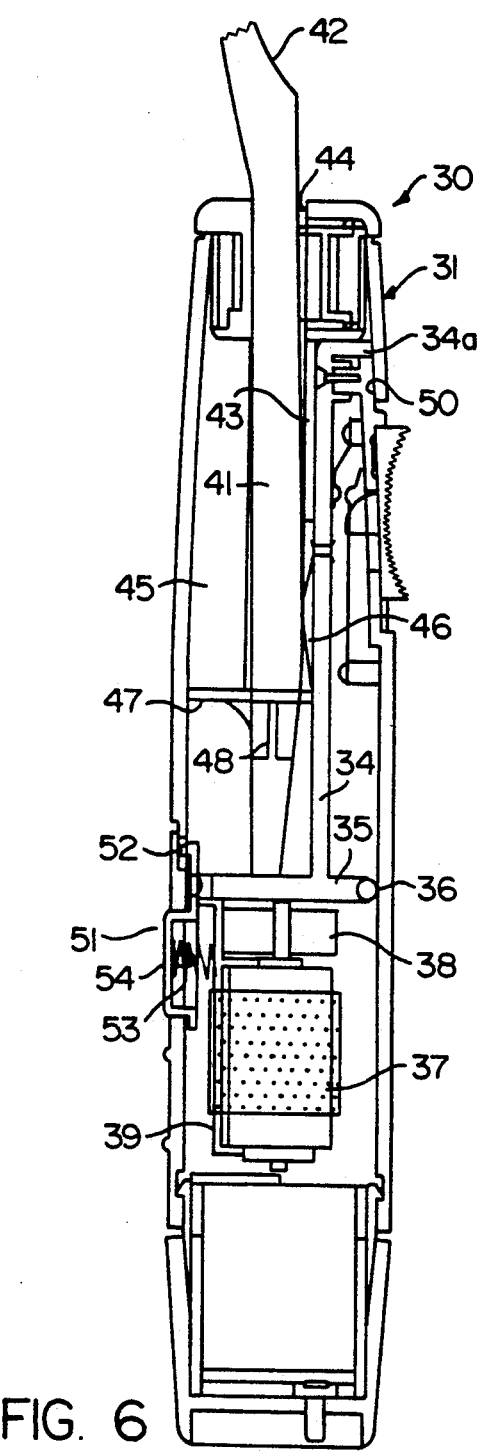
FIG. 6 is a sectional side view of a second embodiment of an electric toothbrush holder in accordance with the invention.
Figure 7:
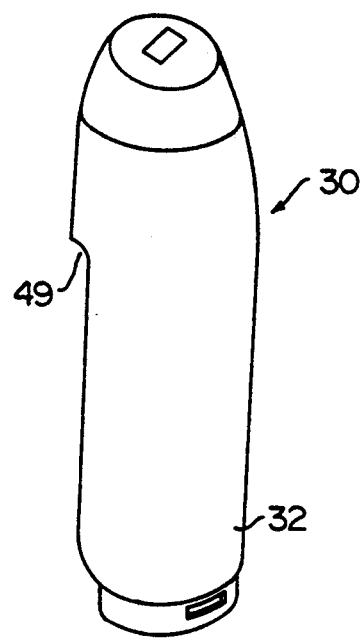
FIG. 7 is a rear side perspective view of the toothbrush holder of FIG. 6, with forward and rear parts thereof separated.
Figure 7:
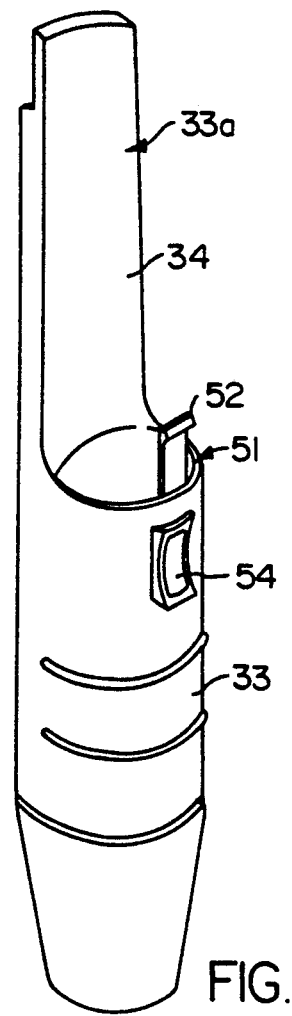

FIGS. 6 and 7 show a second embodiment of an electric toothbrush holder 30 according to the invention, which is principally similar to the first toothbrush holder 10 except that its casing 31 is formed by two separable parts 32 and 33. Forward end 33a of the rear casing portion 33 is in the form of a blade 34 having an inner wall 34 which is integrally connected to a circular plate 35. The circular plate 35 is sealed around its peripheral edge against the inner side of the casing wall by an O-ring 36. The vibration unit formed by an electric motor 37 drivingly supporting an eccentric weight 38 is carried by a bracket 39 depending integrally from below the circular plate 35.

Concerning the forward casing part 32, it provides the forward end of the overall casing 31 including an opening 44 (corresponding to the opening 15), and provides a cavity 45 (corresponding to the cavity 14) for accommodating a handle 41 of an ordinary toothbrush 42. The cavity 45 is defined by a side wall 43 which carries a leaf spring 46 (corresponding to the spring 21). The opposite side of the cavity 45 is defined by the wall of the casing part 32, extending inwardly from which there is a plate 47 having a plurality of springy fingers 48 which are co-operable with the leaf spring 46 to fix the free end of the toothbrush handle 41, as shown in FIG. 6.

The forward casing part 32 has a step 49 to accommodate the blade-like forward end 33a of the rear casing part 33 when the two casing parts 32 and 33 are engaged together. In the engaged condition, the free end of the forward end 33a of the rear casing part 33 enters into a recess 50 provided at the corner of the step 49. The casing parts 32 and 33 are locked together by a latch 51 provided across the circular wall 35, as shown. The latch 51 has a latching member 52 which is resiliently biassed into a locking position by a spring 53 located behind a push-button 54.

For cleaning or washing purpose, the forward casing part 32 is separated from the rear casing part 33 by releasing the latch 51 by pressing the push-button 54, whereas the rear casing part 33 which in practice should be kept away from water remains sealed.

In either toothbrush holder 10 or 30, the cavity 14 or 45 extends from the casing forward end into the casing 11 or 31 for a length at least one-third of the overall length of the casing 11 or 31. This arrangement is understood to ensure a sufficiently tight grip of the toothbrush by the corresponding holder 10 or 30.

The invention has been given by way of example only, and various modifications of and/or alterations to the described embodiments may be made by persons skilled in the art without departing from the scope of the invention as specified in the appended claims.

What is claimed is:

1. An electric toothbrush holder comprising a elongate casing having a forward end and an electric motor vibration unit supported within the casing, the casing forming a elongate cavity having an opening at the forward end of the casing for insertion of the handle of a toothbrush, in which opening there is provided clamping means and a resilient member, said clamping means having at least two clamping surfaces which are resiliently biased relatively together by the resilient member so as to clamp or hold said toothbrush at its handle automatically when the toothbrush handle is inserted into the cavity through the opening;

said clamping means being provided by a fixed clamping element/member and a movable clamping member, the two being resiliently biased relatively together by the resilient member;

the fixed clamping element/member has a flat clamping surface and the movable clamping member has a concave clamping surface facing the flat clamping surface.

2. An electric toothbrush holder as claimed in claim 1, wherein the cavity extends from the casing forward end into the casing for a length at least one-third of the overall length of the casing.

3. An electric toothbrush holder as claimed in claim 1, further comprising auxiliary clamping means which is provided at or adjacent an inner end of the cavity.

4. An electric toothbrush holder as claimed in claim 3, wherein said auxiliary clamping means comprises a leaf spring provided on one side of the cavity and cooperable with the opposite side of the cavity.

5. An electric toothbrush holder as claimed in claim 1, wherein the vibration unit is supported by the innermost end of an internal part of the casing providing the cavity.

6. An electric toothbrush holder as claimed in claim 5, wherein the casing has an external part and an internal part, the internal part of the casing being connected to the external part of the casing at a position only at or near the outer end of the cavity.

7. An electric toothbrush holder comprising a elongate casing having a forward end and an electric motor vibration unit supported within the casing, the casing forming a elongate cavity having an opening at the forward end of the casing for insertion of the handle of a toothbrush, in which opening there is provided clamping means and a resilient member, said clamping means having at least two clamping surfaces which are resiliently biased relatively together by the resilient member so as to clamp or hold said toothbrush at its handle automatically when the toothbrush handle is inserted into the cavity through the opening;

wherein the casing is formed by a forward part carrying the clamping means and a rear part carrying the vibration unit, and the electric toothbrush holder further comprises releasable engaging means for releasably engaging the forward and rear casing parts together such that the forward casing part is separable from the rear casing part for individual cleaning or washing.

8. An electric toothbrush holder comprising a elongate casing having a forward end and an electric motor vibration unit supported within the casing, the casing forming a elongate cavity having an opening at the forward end of the casing for insertion of the handle of a toothbrush, in which opening there is provided clamping means and a resilient member, said clamping means having at least two clamping surfaces which are resiliently biased relatively together by the resilient member so as to clamp or hold said toothbrush at its handle automatically when the toothbrush handle is inserted into the cavity through the opening, and, wherein the resilient member is in the form of a rubber band disposed around the clamping means.

* * * * *